United States Patent [19]

Rosenburg et al.

[11] Patent Number: 4,491,588

[45] Date of Patent: Jan. 1, 1985

[54] TREATMENT OF PSORIASIS AND SEBORRHEIC DERMATITIS WITH IMIDAZOLE ANTIBIOTICS

[75] Inventors: E. William Rosenburg, Memphis; Patricia W. Belew, Germantown, both of Tenn.

[73] Assignee: University of Tennessee Research Corporation, Knoxville, Tenn.

[21] Appl. No.: 474,214

[22] Filed: Mar. 17, 1983

Related U.S. Application Data

[63] Continuation-in-part of Ser. No. 363,845, Mar. 31, 1982, abandoned.

[51] Int. Cl.³ .......................................... A61K 31/415
[52] U.S. Cl. ................................................ 424/273 R
[58] Field of Search ............................ 424/250, 273 R

[56] References Cited

U.S. PATENT DOCUMENTS 4,172,947 10/1979 Warner et al. ...................... 548/346
4,205,071 5/1980 Durant et al. ....................... 424/244
4,358,449 11/1982 Heeres et al. ................... 424/248.58

OTHER PUBLICATIONS

Chemical Abstracts 97:84718d (1982).
"Activation of the Alternative Pathway of Complement by Malassezia Ovalis (Pityrosporum Ovale)", Mycopathologia, vol. 70.3, pp. 187–191 (1980)—Article discusses a mechanism for seborrheic dermatitis.
"Effect of Topical Applications of Heavy Suspensions of Killed Malassezia Ovalis on Rabbit Skin," Mycopathologia, vol. 72, pp. 147–154, (1980)—Article discusses experimentation leading to an explanation of human psoriasis.
"Sabouraud and Rivolta were Right—Seborrheic Dermatitis is Microbial", Cosmetics and Toiletries, Aug. 1981—Article discusses a mechanism for seborrheic dermatitis.

Primary Examiner—Leonard Schenkman
Attorney, Agent, or Firm—Luedeka & Neely

[57] ABSTRACT

A method is provided for treating psoriasis and seborrheic dermatitis in humans by oral administration of an effective, lesion reducing, amount of an imidazole antibiotic.

7 Claims, No Drawings

TREATMENT OF PSORIASIS AND SEBORRHEIC DERMATITIS WITH IMIDAZOLE ANTIBIOTICS

This is a continuation-in-part of application Ser. No. 06/363,845, which was filed on Mar. 31, 1982 now abandoned, and which is assigned to the assignee of this invention.

The present invention relates to methods for the clinical management of patients suffering with the skin diseases of psoriasis and seborrheic dermatitis. In particular, it provides for a new and safe treatment for those diseases by oral administration of imidazole antibiotics.

Psoriasis is a skin disease of unknown cause that produces chronic, recurrent lesions which cause extreme emotional and physical discomfort to patients. Typically, the lesions of psoriasis are round, dry patches of varying size covered by abundant grayish-white scabs. The lesions may cover the entire body, though they are most frequently located around the scalp, body folds and nails.

Seborrheic dermatitis is a common skin disease with clinical similarities to psoriasis. While suggestions have been made over the years that it may be related to microbial factors, its cause is also considered still unknown.

Management of psoriasis and seborrheic dermatitis at this time depends on non-specific agents which are designed to slow down the metabolism of the inflamed epithelial layers of the skin and the use of agents which provide anti-inflammatory effects. Such treatments consist of a local application of corticosteroid products which have a general anti-inflammatory effect on all skin disease but do not produce a permanent or lasting clearing in most cases of psoriasis and seborrheic dermatitis. Other local applications are derivatives of tar or anthralin which work in ways which are not understood. It is assumed in psoriasis that these agents work by inhibiting cell replication and they are classified as cytotoxic.

Several agents are in use for the treatment of seborrheic dermatitis by application to the skin. These topical agents include selenium sulfide, zinc pyridine thiol, and sulphur. The mechanism of action of these agents is not understood either. Current textbooks and reference sources consider them effective by virtue of their general cytotoxic effects on proliferating skin.

Most patients with psoriasis and seborrheic dermatitis would prefer to treat their disease by taking an internal medication rather than enduring the difficulties inherent in topical applications of ointments, creams and lotions. Heretofore there have been no safe and effective specific medications for either psoriasis or seborrheic dermatitis which can be administered orally. Agents which have been used systemically include cortisone derivatives. These work entirely non-specifically, however, and have well-known side-effects which limit their prolonged use. Most authorities feel they should be used sparingly, if at all, in treating either psoriasis or seborrheic dermatitis.

Various cytotoxic agents such as methotrexate and hydroxyurea are used for the control of psoriasis, but these agents, which are designed primarily for use in treatment of cancer, have pronounced antimetabolic effects throughout the body and their use is colored by many cautions. Because of their potential dangers, they are not in general use for most cases of psoriasis and are never used in seborrheic dermatitis.

The phototoxic agent 8-methoxypsoralen is used in combination with administration of ultraviolet light for the treatment of psoriasis but not seborrheic dermatitis. This treatment program, called PUVA, is still under investigation for the treatment of psoriasis. Questions have been raised about the possibility of skin cancer and cataracts resulting from PUVA therapy.

It is accordingly an object of the present invention to provide a method for treating psoriasis and seborrheic dermatitis. It is another object to provide a safe, orally administrable agent for treating psoriasis and seborrheic dermatitis. Various other objects and advantages will be apparent from the following description.

Generally, in accordance with the present invention psoriasis and seborrheic dermatitis in humans are effectively treated by the simple oral administration of an imidazole antibiotic, in an effective, lesion reducing amount, for a period of two to twenty weeks.

While various imidazole antibiotics may be employed, the preferred compounds are selected from the group consisting of ketoconazole [cis-1-acetyl-4-[4-[[2-(2,4-dichlorophenyl)-2-(1H-imidazole-1-ylmethyl)-1,3-dioxolan-4-yl] methoxy] phenyl] piperazine] and metronidazole [1-($\beta$-hydroxyethyl)-2-methyl-5-nitroimidazole].

The administration of the imidazole antibiotics, as pointed out above is oral, usually just prior to meal times, in a daily amount which will eliminate the lesions over the course of the treatment. Depending upon conditions, the total amount may vary from 50 mg. to about 1250 mg. per day and preferably in an amount from 200 mg. to 400 mg. per day.

Ketoconazole is a drug whose main effect on the human organism is that of an antibiotic against various yeasts and fungi. Metronidazole is another antimicrobial imidazole drug which is effective in controlling the growth of anaerobic bacteria. Unlike drugs such as methotrexate, hydroxyurea, 8-methoxypsoralen (plus ultraviolet light) or corticosteroid presently used for systemic administration in psoriasis, these compounds present far fewer safety problems and bring the possibility of neat, safe and effective treatment of psoriasis into the realm of possibility for the first time.

The invention will be better understood from the following examples which are given by way of illustration and not by way of limitation.

EXAMPLE I

Patient has had a thick, scaly psoriasis of the scalp for more than 30 years. Previous treatment with tar shampoos and corticosteroid lotions have not been effective. Administration of ketoconazole, 200 mg. per day, produces a decrease in itching after six to eight weeks and a thinning of the scale after eight to ten weeks. By the end of sixteen weeks, the scalp shows only a minimal tendency to redness and a very fine branny scale.

EXAMPLE 2

The patient of Example 1 has had fingernail changes of psoriasis for many years. At the end of twelve weeks she noticed that her fingernails are also starting to improve and by the end of sixteen weeks there is a 20% improvement in all of her nails. Continued treatment produces further clearing.

EXAMPLE 3

A patient who suffers from sacro-iliitis is forced to lie immobile for long periods on his back. Subsequent to the development of immobility, a florid seborrheic dermatitis eruption appears on his face. It does not improve with applications of corticosteroid creams. The oral administration of ketoconazole is followed by rapid clearing of the redness within two weeks. Sensation of itchiness also disappears.

EXAMPLE 4

A patient has severe, moist, oozing, beefy red psoriasis involving the scalp, the axillary folds, the middle of the chest, the inguinal creases and the gluteal cleft. Administration of 400 mg. a day of ketoconazole produces a beginning of lightening of skin color after three weeks and an improvement of about 70% at the end of six weeks on the body folds and creases. At the end of ten weeks the scalp is starting to improve also.

EXAMPLE 5

A 36 year old man had psoriasis for 3 years. It has responded only partially to conventional external treatment with tar and corticosteroid creams. In addition to his psoriasis, the patient was known to suffer also from ulcerative colitis which had begun 7 years previously, 4 years before his psoriasis appeared. Three years previously, at about the same time his psoriasis appeared, a surgical resection of his colon (colectomy) was performed to control the symptoms of his colitis.

After one month of taking 250 mg. of metronidazole orally four times a day, the patient's psoriasis clears completely, with no local applications of any kind used concomitantly. He reports, also, that the metronidazole produced no increase in his bowel symptoms.

The use of ketoconazole or metronidazole for the treatment of seborrheic dermatitis or psoriasis requires merely taking one or two tablets a day before meals for a period of some two to twenty weeks. No special precautions are required other than the ordinary ones which presently accompany the drugs when used for control of yeast, fungal and bacterial infections. No special laboratory testing of patients is required. Evaluation of the effectiveness of the medication is by simple inspection of the patient and by changes in the amounts of itching present.

Preferably, the total dosage of ketoconazole is from about 200 mg. to about 400 mg. per day. The preferred total dosage of metronidazole is from about 750 mg. to about 1250 mg. per day. In the case of either compound the total dosage is divided into smaller increments which are administered several times per day, usually three or four.

The oral administration of imidazoles on a daily basis produces beneficial effects on psoriasis and seborrheic dermatitis. In psoriasis the improvement begins after a period of one and a half to three months. In seborrheic dermatitis the patients begin seeing less redness, itchiness, and scaling within a period of four to six weeks. The benefits of this treatment occur without the need for applications of ointments or other topical applications. Once the patient is clear there may be prolonged or medium duration of time before the need for retreatment occurs.

While preferred embodiments have been described hereinabove, it will be recognized that there is no intent to limit the invention by such disclosure, but rather it is intended to cover all modifications and variations falling within the spirit and scope of the invention as defined in the appended claims.

We claim:

1. A method of treating psoriasis or seborrheic dermatitis in humans comprising the oral administration of an effective, lesion reducing, amount of an imidazole antibiotic to said humans, said imidazole antibiotic being selected from the group consisting of ketoconazole and metronidazole.

2. The method of claim 1 wherein said imidazole antibiotic is ketoconazole.

3. The method of claim 2 wherein said antibiotic is administered in amounts of from about 200 mg. to about 400 mg. per day.

4. The method of claim 1 wherein said imidazole antibiotic is metronidazole.

5. The method of claim 4 wherein said antibiotic is administered in amounts of from about 750 mg. to about 1250 mg. per day.

6. The method of claim 1 wherein said antibiotic is administered in amounts of from about 50 mg. to about 1250 mg. per day.

7. The method of claim 1 wherein said antibiotic is administered in amounts of from about 200 mg. to about 400 mg. per day.

* * * * *

UNITED STATES PATENT AND TRADEMARK OFFICE
CERTIFICATE OF CORRECTION

PATENT NO.   : 4,491,588

DATED        : January 1, 1985

INVENTOR(S)  : E. William Rosenberg and Patricia W. Belew

It is certified that error appears in the above—identified patent and that said Letters Patent is hereby corrected as shown below:

In the Heading of the Patent, "Rosenburg et al." should read -- Rosenberg et al --.

In the Identification of the Inventors, "E. William Rosenburg" should read -- E. William Rosenberg --.

Signed and Sealed this

Seventh Day of May 1985

[SEAL]

Attest:

DONALD J. QUIGG

Attesting Officer

Acting Commissioner of Patents and Trademarks